(12) United States Patent
Michel et al.

(10) Patent No.: US 10,350,079 B2
(45) Date of Patent: Jul. 16, 2019

(54) TALUS SURFACE IMPLANT

(71) Applicant: Arthrex, Inc., Naples, FL (US)

(72) Inventors: Gerlinde Michel, München (DE); Samuel Bachmaier, Mauern (DE)

(73) Assignee: ARTHREX, INC., Naples, FL (US)

( * ) Notice: Subject to any disclaimer, the term of this patent is extended or adjusted under 35 U.S.C. 154(b) by 788 days.

(21) Appl. No.: 14/453,722

(22) Filed: Aug. 7, 2014

(65) Prior Publication Data

US 2014/0350688 A1 Nov. 27, 2014

Related U.S. Application Data

(63) Continuation of application No. PCT/IB2013/000658, filed on Apr. 12, 2013.

(30) Foreign Application Priority Data

Apr. 12, 2012 (EP) ..................... 12163997

(51) Int. Cl.
*A61F 2/42* (2006.01)
*A61F 2/30* (2006.01)

(52) U.S. Cl.
CPC ........ *A61F 2/4202* (2013.01); *A61F 2/30756* (2013.01); *A61F 2002/30841* (2013.01); *A61F 2002/30878* (2013.01); *A61F 2002/30891* (2013.01); *A61F 2002/4207* (2013.01)

(58) Field of Classification Search
CPC ............ A61F 2/4202; A61F 2002/4207; A61F 2002/30841; A61F 2002/30878
See application file for complete search history.

(56) References Cited

U.S. PATENT DOCUMENTS

| 6,409,767 | B1 * | 6/2002 | Perice | A61F 2/4202 |
| | | | | 623/21.18 |
| 7,534,270 | B2 * | 5/2009 | Ball | A61F 2/4202 |
| | | | | 623/21.18 |
| 2002/0055744 | A1 | 5/2002 | Reiley | |
| 2010/0057216 | A1 * | 3/2010 | Gannoe | A61F 2/4202 |
| | | | | 623/21.18 |
| 2012/0109326 | A1 * | 5/2012 | Perler | A61F 2/4202 |
| | | | | 623/21.18 |

FOREIGN PATENT DOCUMENTS

| EP | 1 097 680 A1 | 5/2001 |
| WO | WO 00/69373 A1 | 11/2000 |
| WO | WO 2006/136940 A2 | 12/2006 |

* cited by examiner

*Primary Examiner* — Brian A Dukert
(74) *Attorney, Agent, or Firm* — Carlson, Gaskey & Olds

(57) ABSTRACT

A talus surface implant has an arc shaped body with a top side interfacing to the tibia and a bottom side having at least one post for interfacing with holes in the talus and a plurality of spikes for interfacing with the surface of the talus. Preferably the implant is double arc shaped.

14 Claims, 5 Drawing Sheets

TALUS SURFACE IMPLANT

PRIORITY CLAIM

This is a continuation of pending International Application No. PCT/IB2013/000658, filed on Apr. 12, 2013, which designates the United States and claims priority to European Application No. 12163997.5, filed on Apr. 12, 2012.

BACKGROUND OF THE INVENTION

1. Field of the Invention

The present invention relates to a talus implant system and a method for surgical reconstitution of the ankle.

2. Description of Relevant Art

The ankle is a synovial hinge joint connecting the distal ends of the tibia and fibula in the lower limb with the proximal end of the talus bone in the foot. For treatment of arthrosis or damage of the joint treatments like ankle arthrodesis and ankle arthroplasty are known. The US patent application publication 2002/0055744 A1 discloses an ankle prosthesis which requires a comparatively complex insertion procedure and massive intrusion into the body of the patient.

US 2010/0057216 A1 discloses a talus resurfacing system, where a plate is fixed to the talus by a screw penetrating through the bone. This through hole is weakening the bone.

WO 2000/69373 discloses an ankle prosthesis, where anchoring in the talus bone is done by two parallel and slightly inclined pins. The talus part is only held together with the tibia part of the implant.

SUMMARY OF THE INVENTION

The embodiments are based on the object of providing an implant and a method for repairing cartilage damage of the talus surface.

In an embodiment, an implant is provided which almost covers the whole proximal cartilage surface of the talus. The implant is arc shaped and adapted to the anatomical shape of the talus. It has a bottom surface which covers the bone of the talus replacing the cartilage. At the bottom surface there are means for anchoring the implant into the bone. The means for anchoring comprise at least one post which is inserted into a hole at the proximal side of the talus. The at least one post preferably is a short stud, which only engages into a blind hole in the surface of the talus. In contrast to the prior art, the plate is not bolted to the bone and in particular a bone weakening through hole in the bone is avoided. Therefore, only a stud hole is required in the bone. Preferably, the at least one post is held by form closure in the hole. Most preferably it does not require a screw or any comparable means for holding the implant to the bone. Preferably two posts are provided. It is further preferred, if the at least one post is close to a front side of the implant which is located anterior (in the direction of the toes). Preferably, the at least one post is in a front section of the plate, the front section comprising the half, most preferably a third of the implant's length to the front side. The at least one post may have a structured surface to accelerate ingrowth of the bone. Furthermore the means for anchoring comprise a plurality of spikes for penetrating into the bone surface. Preferably, the spikes or at least some of the spikes are in the rear section of the plate, the rear section including half, most preferably a third of the implant's length to the rear side. Opposing to the bottom surface, the implant has a top surface which interfaces with the Tibia. Alternatively the top surface may interface with a tibia implant. Preferably this surface may have been treated to obtain a low friction and or may have a low friction coating. Preferably the implant has a length measured between the front side and rear side in a range from 25 to 45 mm. It further has a preferred width measured as the largest extension between the inner side and outer side between 25 and 40 mm. Preferably, the dimensions of the implant are adapted to the talus size.

Preferably the implant is arc shaped having an axis below the bottom side and going approximately parallel to the implant surface from the inner side to the outer side. The arc preferably covers an angle between 80 degrees and 110 degrees, most preferably of 95 degrees. Due to the arc shaped implant, the at least one post and the spikes, the implant is held at its place. If there would be a movement of the plate out of the holes, into direction (or along a center axis) of the at least one post, the spikes would generate friction to prevent such a movement. The plate is further supported by the pressure of the tibia, the muscles and ligaments. With the tibia in place on the surface of the implant, it is no more possible for the posts to slide out of their holes. Therefore, the implant is looked at its position. Preferably, the length of the at least one post is between 3 mm and 20 mm, most preferably between 5 mm and 10 mm longer than the maximum distance between the tibia and the talus. Such a maximum distance may be measured at an unloaded leg. It is further preferred, if each post is at an approximately right angle, preferably at a right angle to the surface of the implant at the location of the post.

Most preferably the implant is further arc shaped having an axis above the top side and under a right angle to the first axis. It may have the shape of a cylinder segment which is bent over an axis under a right angle to the center axis of the cylinder.

Preferably the implant is made of one of cobalt, chrome, titanium, surgical steel, PEEK or any other suitable material.

In a further embodiment a cushion is provided on the top surface. This is preferably for decreasing friction and for damping. The cushion may be made of a material like polycarbonate-urethane (PCU).

In another embodiment the bottom side of the implant comprises a plurality of planar segments. These simplify preparation of the bone, as multiple planes can be easier machined than a complex arc shaped surface.

A further embodiment is a trial implant which may be used as a drilling gauge and which may also be used for testing the fit of the implant. It preferably has at least one hole to allow drilling of the at least one hole into the talus which is required for holding the at least one post of the implant. Accordingly the at least one hole is located at the position of the at least one post of the implant. Most preferably the trial implant has at least two such holes. Furthermore it is preferred, if the trial implant has at least one insertion bracket which allows easy insertion and removal of the implant. Furthermore it is preferred, if the implant has at least one trial fixation hole through which posts or wires may be fixed to the bone of the talus holding the trial implant in place. Preferably the implant has two trial fixation holes.

Another embodiment is a method for treating of arthrosis or damage of the joint. The method comprises the steps of removing the proximal cartilage of the talus, drilling or machining at least one hole suitable to accommodate the at least one post of an implant into the bone surface and to insert the implant into the joint by placing the at least one post into the at least one hole.

BRIEF DESCRIPTION OF THE DRAWINGS

In the following, the invention will be described by way of example, without limitation of the general inventive concept, on examples of embodiment and with reference to the drawings.

Figure 1:
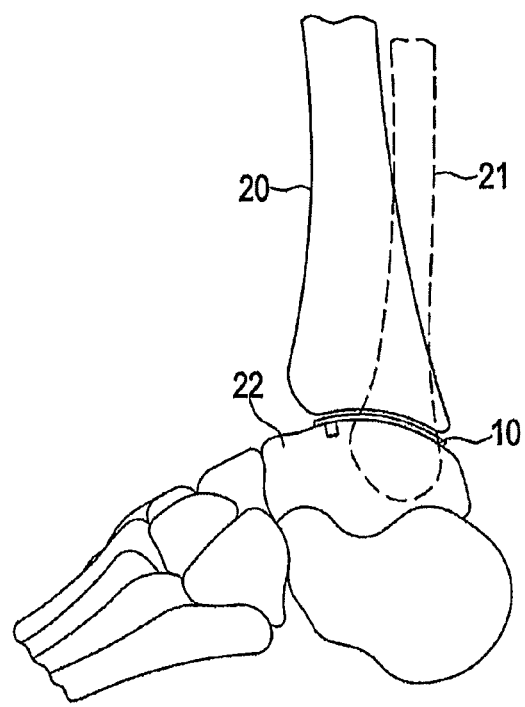
FIG. 1 shows a talus surface implant as implanted.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

FIG. 1 shows in details the bones of a human ankle. The ankle is a synovial hinge joint connecting the distal ends of the tibia 20 and fibula 21 in the lower limb with the proximal end of the talus 22 bone in the foot. The talus surface implant 10 is located at the proximal side of the talus.

Figure 2:
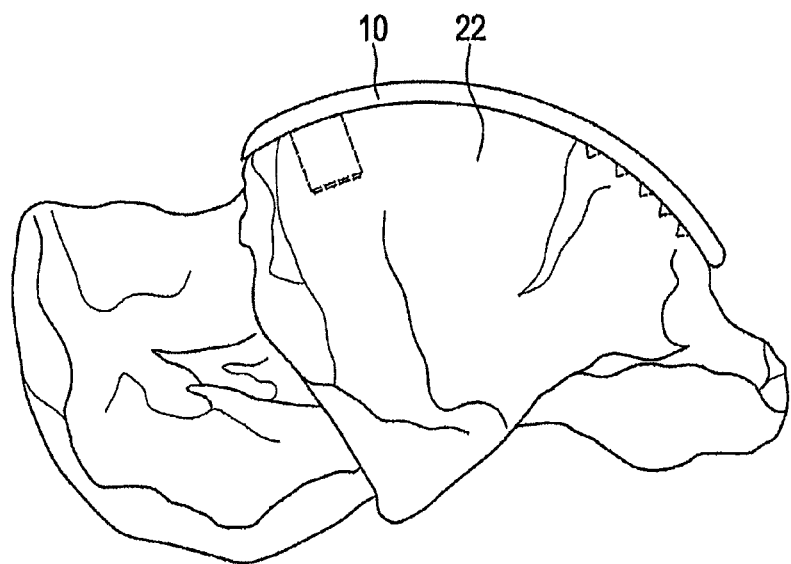
FIG. 2 shows the implant on the talus in detail.

FIG. 2 shows the talus implant 10 located on the proximal side of the talus 22. One of the posts 17 for holding the implant and some of the spikes 19 are also shown.

Figure 3:
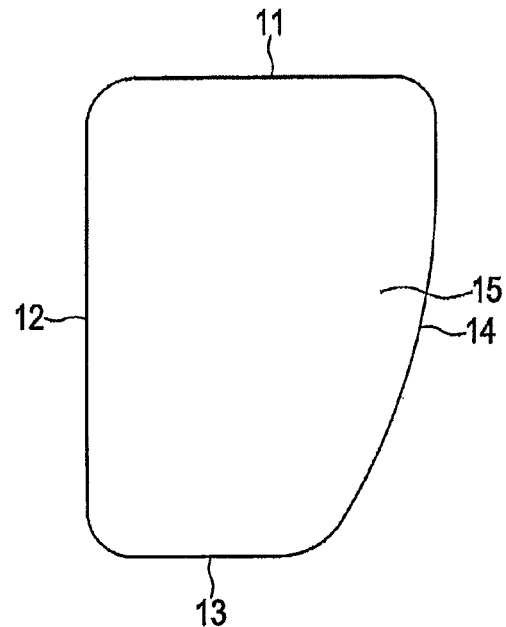
FIG. 3 shows the implant in a top view.

FIG. 3 shows the implant 10 in a top view. The implant has a top side 15 which interfaces with the tibia. The outer contour of the implant is defined by a front side 11 directed anterior (towards the toes) and opposed thereto (posterior) a shorter rear side 13. Between these is an inner side 12 and opposed thereto an outer side 14. The outer side 14 is slightly curved to adapt to the surface of the talus from the longer front side 11 to the shorter rear side 13.

Figure 4:
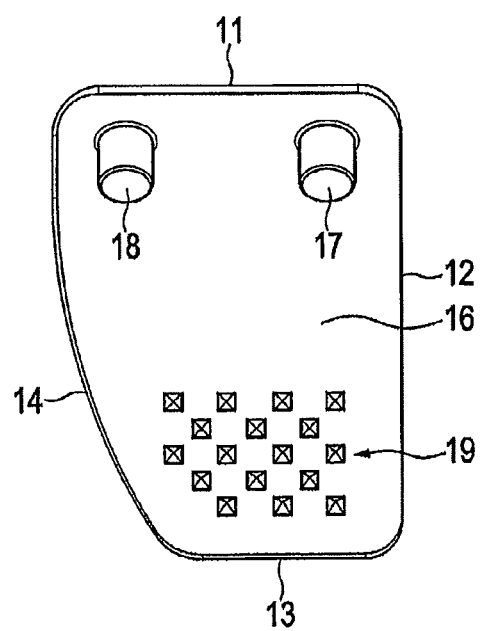
FIG. 4 shows the implant in bottom view.

In FIG. 4 the implant is shown in a bottom view. It shows a bottom side 16 having an inner post 17 and an outer post 18, which are both to be inserted into holes of the talus. Furthermore spikes 19 are shown which improve the mechanical contact between the implant and the bone surface by penetrating into the bone. This view is under an approximately right angle to the inner surface 16 in the area of the spikes 19.

Figure 5:
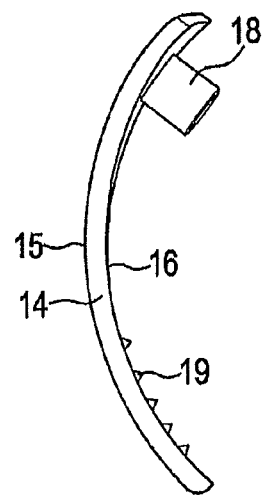
FIG. 5 shows a side view of the implant.

In FIG. 5 a side view on the outer side 14 is shown. It shows the arc shape under a first axis.

Figure 6:
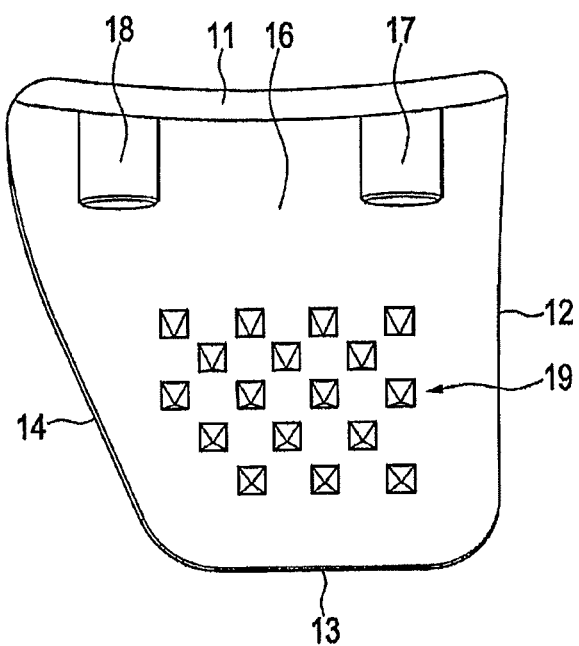
FIG. 6 shows a front view of the implant.

In FIG. 6 a front view of the implant is shown under a right angle to the front side 11. Here the arc shape of the implant under the second axis can be seen.

Figure 7:
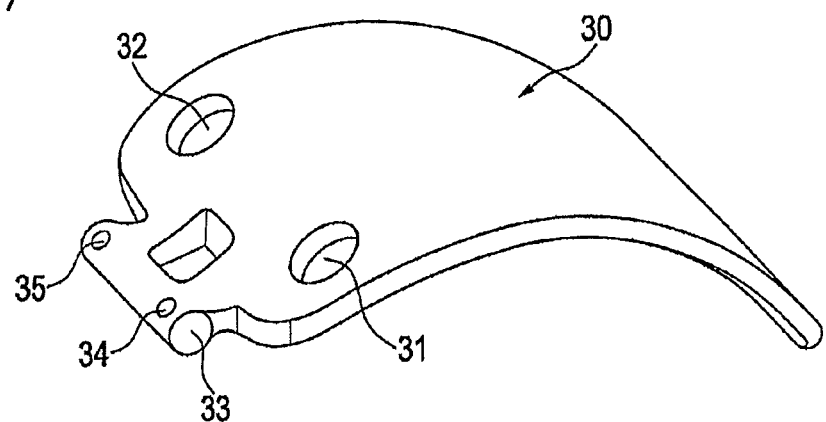
FIG. 7 shows a trial implant.

FIG. 7 shows a trial implant 30. Such a trial implant may be used as a drilling gauge for drilling holes into the talus surface. It may further be used to figure out the correct size of an implant to be implanted. This trial implant has an outer drilling hole 31 and an inner drilling hole 32 through which holes may be drilled into the surface of the talus for inserting posts of the implant. Furthermore the trial implant has an insertion bracket 33 which allows insertion and removal of the implant. There may be a specific tool for interfacing with the insertion bracket. The inner trial fixation hole 34 and the outer trial fixation hole 35 allow placing of posts through the holes into the bone of the talus holding the trial implant in place, specifically when drilling the holes into the talus.

Figure 8:
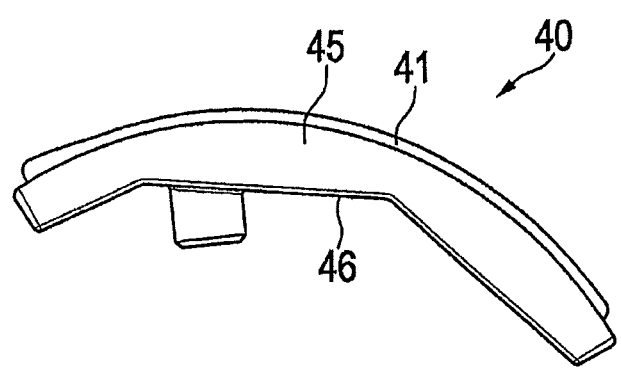
FIG. 8 shows a modified embodiment of an implant.

In FIG. 8 a modified embodiment 40 of an implant is shown. Here a cushion 41 is provided at the surface of top side 45. This is preferably for decreasing friction and for providing some damping. The cushion may be made of a material like polycarbonate-urethane (PCU). Such a cushion may also be applied to all previous shown embodiments. Furthermore, the bottom side 46 comprises three planar segments which allow for easier preparing of the bone. Alternatively, it may comprise any other number of planar segments.

Figure 9:
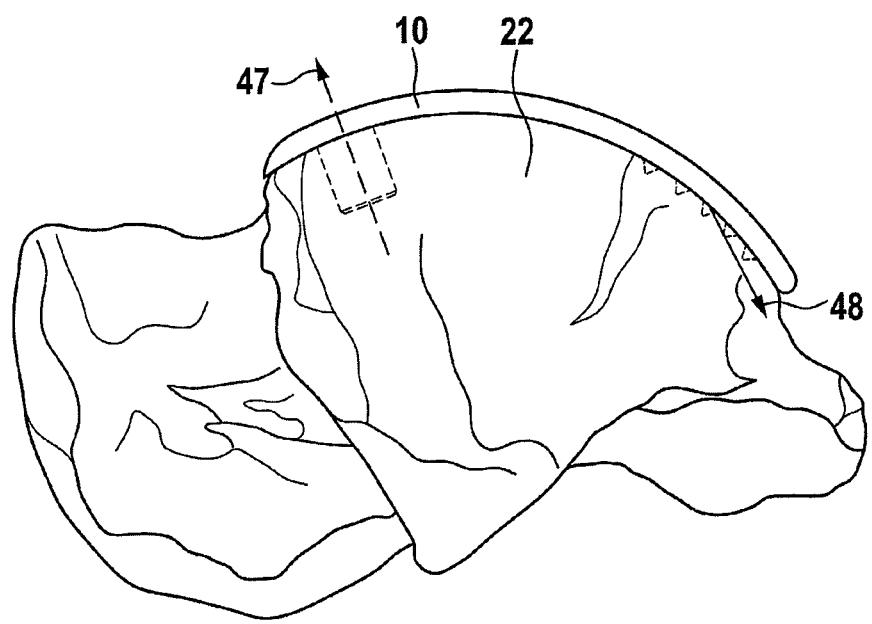
FIG. 9 shows the holding force of the spikes.

In FIG. 9, a force holding the plate in place is shown. Assuming the plate may be pulled off the talus, this may only be done in direction 47 of the post. For this case, the spikes generate a counterforce 48 and hold the plate in place. Holding the plate in place is further supported by the tibia bearing the weight of the person and pressing on the plate.

It will be appreciated to those skilled in the art having the benefit of this disclosure that this invention is believed to provide a talus surface implant and a method for using this implant. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A talus surface implant having an arc shaped body with a top side configured for interfacing to the tibia, a bottom side, a front section and a rear section, the bottom side having at least one post configured for interfacing with holes in a talus and a plurality of spikes configured for interfacing with the surface of the talus, wherein the height of the at least one post does not exceed the thickness of the talus, the at least one post is arranged in the front section of the arc shaped body, the front section having less than half of the length of the arc shaped body, the front section being oriented anterior, the plurality of spikes is arranged in the rear section of the arc shaped body, the rear section having less than half of the length of the arc shaped body, the rear section being oriented posterior.

2. The talus surface implant according to claim 1, wherein the implant is arc shaped having an axis below the bottom side and going approximately parallel to the implant surface from an inner side to an outer side.

3. The talus surface implant according to claim 2, wherein the implant is arc shaped having a second axis above the top side under a right angle to the first axis.

4. The talus surface implant according to claim 1, wherein the implant has two posts configured for interfacing with holes in the talus.

5. The talus surface implant according to claim 1, wherein the front section has less than one third of the length of the arc shaped body.

6. The talus surface implant according to claim 1, wherein the rear section has less than one third of the length of the arc shaped body.

7. The talus surface implant according to claim 1, wherein the implant has a bottom side including a plurality of planar segments.

8. The talus surface implant according to claim 1, wherein the implant has a cushion provided on its top side, the cushion being separate from the implant.

9. A method for treating of arthrosis or damage of a joint including the steps of: removing the proximal cartilage of a talus, using a trial implant as a gauge to prepare the talus for receiving an implant by drilling or machining at least one hole suitable to accommodate at least one post of the implant into the bone surface, and inserting the implant into the joint by placing the at least one post into the at least one hole, and wherein a height of the at least one post does not exceed the thickness of the talus.

10. The method according to claim 9, comprising testing a fit of the implant with the aid of the trial implant.

11. The method according to claim 9, comprising removing the trial implant prior to inserting the implant into the joint.

12. The method according to claim 9, wherein the implant includes a cushion that is provided on a top side of the implant, the cushion being separate from the implant.

13. The method according to claim 9, wherein the implant includes a plurality of spikes.

14. The method according to claim 13, wherein the plurality of spikes are is arranged in a rear section of an arc shaped body of the implant and the at least one post is arranged in a front section of the arc shaped body.

* * * * *